(12) United States Patent
Nordstrom et al.

(10) Patent No.: US 7,499,740 B2
(45) Date of Patent: *Mar. 3, 2009

(54) TECHNIQUES FOR DETECTING HEART PULSES AND REDUCING POWER CONSUMPTION IN SENSORS

(75) Inventors: Brad Nordstrom, Alameda, CA (US); William Shea, Livermore, CA (US); Ethan Petersen, Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 72 days.

This patent is subject to a terminal disclaimer.

(21) Appl. No.: 11/650,861

(22) Filed: Jan. 8, 2007

(65) Prior Publication Data

US 2007/0208240 A1    Sep. 6, 2007

Related U.S. Application Data

(63) Continuation of application No. 10/787,851, filed on Feb. 25, 2004, now Pat. No. 7,162,288.

(51) Int. Cl.
*A61B 5/1455* (2006.01)
(52) U.S. Cl. .................................... 600/323
(58) Field of Classification Search ................ 600/300, 600/309, 322, 323, 324; 356/41; 359/239
See application file for complete search history.

(56) References Cited

U.S. PATENT DOCUMENTS

| | | | |
|---|---|---|---|
| 3,403,555 | A | 10/1968 | Versaci et al. |
| 3,536,545 | A | 10/1970 | Traynor et al. |
| D222,454 | S | 10/1971 | Beeber |
| 3,721,813 | A | 3/1973 | Condon et al. |
| 4,098,772 | A | 7/1978 | Bonk et al. |
| D250,275 | S | 11/1978 | Bond |
| D251,387 | S | 3/1979 | Ramsey et al. |

(Continued)

FOREIGN PATENT DOCUMENTS

DE    3405444    8/1985

(Continued)

OTHER PUBLICATIONS

U.S. Appl. No. 11/525,636, filed Sep. 22, 2006, Hoarau.

(Continued)

*Primary Examiner*—Eric F Winakur
*Assistant Examiner*—Etsub D Berhanu

(57) ABSTRACT

Low power techniques for sensing cardiac pulses in a signal from a sensor are provided. A pulse detection block senses the sensor signal and determines its signal-to-noise ratio. After comparing the signal-to-noise ratio to a threshold, the drive current of light emitting elements in the sensor is dynamically adjusted to reduce power consumption while maintaining the signal-to-noise ratio at an adequate level. The signal component of the sensor signal can be measured by identifying systolic transitions. The systolic transitions are detected using a maximum and minimum derivative averaging scheme. The moving minimum and the moving maximum are compared to the scaled sum of the moving minimum and moving maximum to identify the systolic transitions. Once the signal component has been identified, the signal component is compared to a noise component to calculate the signal-to-noise ratio.

29 Claims, 3 Drawing Sheets

U.S. PATENT DOCUMENTS

| | | |
|---|---|---|
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynksi |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |

| | | | | | |
|---|---|---|---|---|---|
| 5,297,548 A | 3/1994 | Pologe | 5,520,177 A | 5/1996 | Ogawa et al. |
| 5,299,120 A | 3/1994 | Kaestle | 5,521,851 A | 5/1996 | Wei et al. |
| 5,299,570 A | 4/1994 | Hatschek | 5,522,388 A | 6/1996 | Ishikawa et al. |
| 5,309,908 A | 5/1994 | Friedman et al. | 5,524,617 A | 6/1996 | Mannheimer |
| 5,311,865 A | 5/1994 | Mayeux | 5,529,064 A | 6/1996 | Rall et al. |
| 5,313,940 A | 5/1994 | Fuse et al. | 5,533,507 A | 7/1996 | Potratz et al. |
| 5,323,776 A | 6/1994 | Blakely et al. | 5,551,423 A | 9/1996 | Sugiura |
| 5,329,922 A | 7/1994 | Atlee, III | 5,551,424 A | 9/1996 | Morrison et al. |
| 5,337,744 A | 8/1994 | Branigan | 5,553,614 A | 9/1996 | Chance |
| 5,339,810 A | 8/1994 | Ivers et al. | 5,553,615 A | 9/1996 | Carim et al. |
| 5,343,818 A | 9/1994 | McCarthy et al. | 5,555,882 A | 9/1996 | Richardson et al. |
| 5,343,869 A | 9/1994 | Pross et al. | 5,558,096 A | 9/1996 | Palatnik |
| 5,348,003 A | 9/1994 | Caro | 5,560,355 A | 10/1996 | Merchant et al. |
| 5,348,004 A | 9/1994 | Hollub et al. | 5,564,417 A | 10/1996 | Chance |
| 5,348,005 A | 9/1994 | Merrick et al. | 5,575,284 A | 11/1996 | Athan et al. |
| 5,349,519 A | 9/1994 | Kaestle | 5,575,285 A | 11/1996 | Takanashi et al. |
| 5,349,952 A | 9/1994 | McCarthy et al. | 5,577,500 A | 11/1996 | Potratz |
| 5,349,953 A | 9/1994 | McCarthy et al. | 5,582,169 A | 12/1996 | Oda et al. |
| 5,351,685 A | 10/1994 | Potratz | 5,584,296 A | 12/1996 | Cui et al. |
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,619,992 A | 4/1997 | Guthrie et al. |
| 5,372,136 A | 12/1994 | Steuer et al. | 5,626,140 A | 5/1997 | Feldman et al. |
| 5,377,675 A | 1/1995 | Ruskewicz et al. | 5,629,992 A | 5/1997 | Amersfoort et al. |
| 5,385,143 A | 1/1995 | Aoyagi | 5,630,413 A | 5/1997 | Thomas et al. |
| 5,387,122 A | 2/1995 | Goldberger et al. | 5,632,272 A | 5/1997 | Diab et al. |
| 5,390,670 A | 2/1995 | Centa et al. | 5,632,273 A | 5/1997 | Suzuki |
| 5,392,777 A | 2/1995 | Swedlow et al. | 5,634,459 A | 6/1997 | Gardosi |
| 5,398,680 A | 3/1995 | Polson et al. | 5,638,593 A | 6/1997 | Gerhardt et al. |
| 5,402,777 A | 4/1995 | Warring et al. | 5,638,816 A | 6/1997 | Kiani-Azarbayjany et al. |
| 5,402,779 A | 4/1995 | Chen et al. | 5,638,818 A | 6/1997 | Diab et al. |
| 5,411,023 A | 5/1995 | Morris, Sr. et al. | 5,645,060 A | 7/1997 | Yorkey et al. |
| 5,411,024 A | 5/1995 | Thomas et al. | 5,645,440 A | 7/1997 | Tobler et al. |
| 5,413,099 A | 5/1995 | Schmidt et al. | 5,660,567 A | 8/1997 | Nierlich et al. |
| 5,413,100 A | 5/1995 | Barthelemy et al. | 5,662,105 A | 9/1997 | Tien |
| 5,413,101 A | 5/1995 | Sugiura | 5,662,106 A | 9/1997 | Swedlow et al. |
| 5,413,102 A | 5/1995 | Schmidt et al. | 5,664,270 A | 9/1997 | Bell et al. |
| 5,417,207 A | 5/1995 | Young et al. | 5,666,952 A | 9/1997 | Fuse et al. |
| 5,421,329 A | 6/1995 | Casciani et al. | 5,671,529 A | 9/1997 | Nelson |
| 5,425,360 A | 6/1995 | Nelson | 5,673,692 A | 10/1997 | Schulze et al. |
| 5,425,362 A | 6/1995 | Siker et al. | 5,673,693 A | 10/1997 | Solenberger |
| 5,427,093 A | 6/1995 | Ogawa et al. | 5,676,139 A | 10/1997 | Goldberger et al. |
| 5,429,128 A | 7/1995 | Cadell et al. | 5,676,141 A | 10/1997 | Hollub |
| 5,429,129 A | 7/1995 | Lovejoy et al. | 5,678,544 A | 10/1997 | DeLonzor et al. |
| 5,431,159 A | 7/1995 | Baker et al. | 5,680,857 A | 10/1997 | Pelikan et al. |
| 5,431,170 A | 7/1995 | Mathews | 5,685,299 A | 11/1997 | Diab et al. |
| 5,437,275 A | 8/1995 | Amundsen et al. | 5,685,301 A | 11/1997 | Klomhaus |
| 5,438,986 A | 8/1995 | Disch et al. | 5,687,719 A | 11/1997 | Sato et al. |
| 5,448,991 A | 9/1995 | Polson et al. | 5,687,722 A | 11/1997 | Tien et al. |
| 5,452,717 A | 9/1995 | Branigan et al. | 5,692,503 A | 12/1997 | Kuenstner |
| 5,465,714 A | 11/1995 | Scheuing | 5,692,505 A | 12/1997 | Fouts |
| 5,469,845 A | 11/1995 | DeLonzor et al. | 5,709,205 A | 1/1998 | Bukta |
| RE35,122 E | 12/1995 | Corenman et al. | 5,713,355 A | 2/1998 | Richardson et al. |
| 5,482,034 A | 1/1996 | Lewis et al. | 5,724,967 A | 3/1998 | Venkatachalam |
| 5,482,036 A | 1/1996 | Diab et al. | 5,727,547 A | 3/1998 | Levinson et al. |
| 5,485,847 A | 1/1996 | Baker, Jr. | 5,730,124 A | 3/1998 | Yamauchi |
| 5,490,505 A | 2/1996 | Diab et al. | 5,731,582 A | 3/1998 | West |
| 5,490,523 A | 2/1996 | Isaacson et al. | D393,830 S | 4/1998 | Tobler et al. |
| 5,491,299 A | 2/1996 | Naylor et al. | 5,743,260 A | 4/1998 | Chung et al. |
| 5,494,032 A | 2/1996 | Robinson et al. | 5,743,262 A | 4/1998 | Lepper, Jr. et al. |
| 5,494,043 A | 2/1996 | O'Sullivan et al. | 5,743,263 A | 4/1998 | Baker, Jr. |
| 5,497,771 A | 3/1996 | Rosenheimer | 5,746,206 A | 5/1998 | Mannheimer |
| 5,499,627 A | 3/1996 | Steuer et al. | 5,746,697 A | 5/1998 | Swedlow et al. |
| 5,503,148 A | 4/1996 | Pologe et al. | 5,752,914 A | 5/1998 | DeLonzor et al. |
| 5,505,199 A | 4/1996 | Kim | 5,755,226 A | 5/1998 | Carim et al. |
| 5,507,286 A | 4/1996 | Solenberger | 5,758,644 A | 6/1998 | Diab et al. |
| 5,511,546 A | 4/1996 | Hon | 5,760,910 A | 6/1998 | Lepper, Jr. et al. |
| 5,517,988 A | 5/1996 | Gerhard | 5,766,125 A | 6/1998 | Aoyagi et al. |

| | | | | | |
|---|---|---|---|---|---|
| 5,766,127 A | 6/1998 | Pologe et al. | 5,924,982 A | 7/1999 | Chin |
| 5,769,785 A | 6/1998 | Diab et al. | 5,924,985 A | 7/1999 | Jones |
| 5,772,587 A | 6/1998 | Gratton et al. | 5,934,277 A | 8/1999 | Mortz |
| 5,774,213 A | 6/1998 | Trebino et al. | 5,934,925 A | 8/1999 | Tobler et al. |
| 5,776,058 A | 7/1998 | Levinson et al. | 5,940,182 A | 8/1999 | Lepper, Jr. et al. |
| 5,776,059 A | 7/1998 | Kaestle | 5,954,644 A | 9/1999 | Dettling et al. |
| 5,779,630 A | 7/1998 | Fein et al. | 5,957,840 A | 9/1999 | Terasawa et al. |
| 5,779,631 A | 7/1998 | Chance | 5,960,610 A | 10/1999 | Levinson et al. |
| 5,782,237 A | 7/1998 | Casciani et al. | 5,961,450 A | 10/1999 | Merchant et al. |
| 5,782,756 A | 7/1998 | Mannheimer | 5,961,452 A | 10/1999 | Chung et al. |
| 5,782,757 A | 7/1998 | Diab et al. | 5,964,701 A | 10/1999 | Asada et al. |
| 5,782,758 A | 7/1998 | Ausec et al. | 5,971,930 A | 10/1999 | Elghazzawi |
| 5,786,592 A | 7/1998 | Hök | 5,978,691 A | 11/1999 | Mills |
| 5,788,634 A | 8/1998 | Suda et al. | 5,978,693 A | 11/1999 | Hamilton et al. |
| 5,790,729 A | 8/1998 | Pologe et al. | 5,983,120 A | 11/1999 | Groner et al. |
| 5,792,052 A | 8/1998 | Isaacson et al. | 5,983,122 A | 11/1999 | Jarman et al. |
| 5,795,292 A | 8/1998 | Lewis et al. | 5,987,343 A | 11/1999 | Kinast |
| 5,797,841 A | 8/1998 | DeLonzor et al. | 5,991,648 A | 11/1999 | Levin |
| 5,800,348 A | 9/1998 | Kaestle | 5,995,855 A | 11/1999 | Kiani et al. |
| 5,800,349 A | 9/1998 | Isaacson et al. | 5,995,856 A | 11/1999 | Mannheimer et al. |
| 5,803,910 A | 9/1998 | Potratz | 5,995,858 A | 11/1999 | Kinast |
| 5,807,246 A | 9/1998 | Sakaguchi et al. | 5,995,859 A | 11/1999 | Takahashi |
| 5,807,247 A | 9/1998 | Merchant et al. | 5,997,343 A | 12/1999 | Mills et al. |
| 5,807,248 A | 9/1998 | Mills | 5,999,834 A | 12/1999 | Wang et al. |
| 5,810,723 A | 9/1998 | Aldrich | 6,002,952 A | 12/1999 | Diab et al. |
| 5,810,724 A | 9/1998 | Gronvall | 6,005,658 A | 12/1999 | Kaluza et al. |
| 5,813,980 A | 9/1998 | Levinson et al. | 6,006,120 A | 12/1999 | Levin |
| 5,817,008 A | 10/1998 | Rafert et al. | 6,011,985 A | 1/2000 | Athan et al. |
| 5,817,009 A | 10/1998 | Rosenheimer et al. | 6,011,986 A | 1/2000 | Diab et al. |
| 5,817,010 A | 10/1998 | Hibl | 6,014,576 A | 1/2000 | Raley et al. |
| 5,818,985 A | 10/1998 | Merchant et al. | 6,018,673 A | 1/2000 | Chin et al. |
| 5,820,550 A | 10/1998 | Polson et al. | 6,018,674 A | 1/2000 | Aronow |
| 5,823,950 A | 10/1998 | Diab et al. | 6,022,321 A | 2/2000 | Amano et al. |
| 5,823,952 A | 10/1998 | Levinson et al. | 6,023,541 A | 2/2000 | Merchant et al. |
| 5,827,179 A | 10/1998 | Lichter et al. | 6,026,312 A | 2/2000 | Shemwell et al. |
| 5,827,182 A | 10/1998 | Raley et al. | 6,026,314 A | 2/2000 | Amerov et al. |
| 5,829,439 A | 11/1998 | Yokosawa et al. | 6,031,603 A | 2/2000 | Fine et al. |
| 5,830,135 A | 11/1998 | Bosque et al. | 6,035,223 A | 3/2000 | Baker, Jr. |
| 5,830,136 A | 11/1998 | DeLonzor et al. | 6,036,642 A | 3/2000 | Diab et al. |
| 5,830,137 A | 11/1998 | Scharf | 6,041,247 A | 3/2000 | Weckstrom et al. |
| 5,839,439 A | 11/1998 | Nierlich et al. | 6,044,283 A | 3/2000 | Fein et al. |
| RE36,000 E | 12/1998 | Swedlow et al. | 6,047,201 A | 4/2000 | Jackson, III |
| 5,842,979 A | 12/1998 | Jarman et al. | 6,055,447 A | 4/2000 | Well |
| 5,842,981 A | 12/1998 | Larsen et al. | 6,061,584 A | 5/2000 | Lovejoy et al. |
| 5,842,982 A | 12/1998 | Mannheimer | 6,064,898 A | 5/2000 | Aldrich |
| 5,846,190 A | 12/1998 | Woehrle | 6,064,899 A | 5/2000 | Fein et al. |
| 5,851,178 A | 12/1998 | Aronow | 6,067,462 A | 5/2000 | Diab et al. |
| 5,851,179 A | 12/1998 | Ritson et al. | 6,073,038 A | 6/2000 | Wang et al. |
| 5,853,364 A | 12/1998 | Baker, Jr. et al. | 6,078,829 A | 6/2000 | Uchida |
| 5,860,919 A | 1/1999 | Kiani-Azarbayjany et al. | 6,078,833 A | 6/2000 | Hueber |
| 5,865,736 A | 2/1999 | Baker, Jr. et al. | 6,081,735 A | 6/2000 | Diab et al. |
| 5,879,294 A | 3/1999 | Anderson et al. | 6,083,157 A | 7/2000 | Noller |
| 5,885,213 A | 3/1999 | Richardson et al. | 6,083,172 A | 7/2000 | Baker, Jr. et al. |
| 5,890,929 A | 4/1999 | Mills et al. | 6,088,607 A | 7/2000 | Diab et al. |
| 5,891,021 A | 4/1999 | Dillon et al. | 6,094,592 A | 7/2000 | Yorkey et al. |
| 5,891,022 A | 4/1999 | Pologe | 6,095,974 A | 8/2000 | Shemwell et al. |
| 5,891,024 A | 4/1999 | Jarman et al. | 6,104,938 A | 8/2000 | Huiku et al. |
| 5,891,025 A | 4/1999 | Buschmann et al. | 6,104,939 A | 8/2000 | Groner |
| 5,891,026 A | 4/1999 | Wang et al. | 6,112,107 A | 8/2000 | Hannula |
| 5,902,235 A | 5/1999 | Lewis et al. | 6,113,541 A | 9/2000 | Dias et al. |
| 5,910,108 A | 6/1999 | Solenberger | 6,115,621 A | 9/2000 | Chin |
| 5,911,690 A | 6/1999 | Rall | 6,122,535 A | 9/2000 | Kaestle et al. |
| 5,912,656 A | 6/1999 | Tham et al. | 6,133,994 A | 10/2000 | Mathews et al. |
| 5,913,819 A | 6/1999 | Taylor et al. | 6,135,952 A | 10/2000 | Coetzee |
| 5,916,154 A | 6/1999 | Hobbs et al. | 6,144,444 A | 11/2000 | Haworth et al. |
| 5,916,155 A | 6/1999 | Levinson et al. | 6,144,867 A | 11/2000 | Walker et al. |
| 5,919,133 A | 7/1999 | Taylor et al. | 6,144,868 A | 11/2000 | Parker |
| 5,919,134 A | 7/1999 | Diab | 6,149,481 A | 11/2000 | Wang et al. |
| 5,920,263 A | 7/1999 | Huttenhoff et al. | 6,151,107 A | 11/2000 | Schöllerman et al. |
| 5,921,921 A | 7/1999 | Potratz et al. | 6,151,516 A | 11/2000 | Kiani-Azarbayjani et al. |
| 5,922,607 A | 7/1999 | Bernreuter | 6,151,518 A | 11/2000 | Hayashi |
| 5,924,979 A | 7/1999 | Swedlow et al. | 6,152,754 A | 11/2000 | Gerhardt et al. |
| 5,924,980 A | 7/1999 | Coetzee | 6,154,667 A | 11/2000 | Miura et al. |

| Patent No. | Date | Inventor(s) | Patent No. | Date | Inventor(s) |
|---|---|---|---|---|---|
| 6,157,850 A | 12/2000 | Diab et al. | 6,393,311 B1 | 5/2002 | Edgar, Jr. et al. |
| 6,159,147 A | 12/2000 | Lichter | 6,397,091 B2 | 5/2002 | Diab et al. |
| 6,163,715 A | 12/2000 | Larsen et al. | 6,397,092 B1 | 5/2002 | Norris et al. |
| 6,165,005 A | 12/2000 | Mills et al. | 6,397,093 B1 | 5/2002 | Aldrich |
| 6,173,196 B1 | 1/2001 | Delonzor et al. | 6,400,971 B1 | 6/2002 | Finarov et al. |
| 6,178,343 B1 | 1/2001 | Bindszus et al. | 6,400,972 B1 | 6/2002 | Fine |
| 6,179,159 B1 | 1/2001 | Gurley | 6,400,973 B1 | 6/2002 | Winter |
| 6,181,958 B1 | 1/2001 | Steuer et al. | 6,402,690 B1 | 6/2002 | Rhee et al. |
| 6,181,959 B1 | 1/2001 | Schöllerman et al. | 6,408,198 B1 | 6/2002 | Hanna et al. |
| 6,184,521 B1 | 2/2001 | Coffin, IV et al. | 6,411,832 B1 | 6/2002 | Guthermann |
| 6,188,470 B1 | 2/2001 | Grace | 6,411,833 B1 | 6/2002 | Baker, Jr. et al. |
| 6,192,260 B1 | 2/2001 | Chance | 6,421,549 B1 | 7/2002 | Jacques |
| 6,195,575 B1 | 2/2001 | Levinson | 6,430,423 B2 | 8/2002 | DeLonzor et al. |
| 6,198,951 B1 | 3/2001 | Kosuda et al. | 6,430,513 B1 | 8/2002 | Wang et al. |
| 6,206,830 B1 | 3/2001 | Diab et al. | 6,430,525 B1 | 8/2002 | Weber et al. |
| 6,213,952 B1 | 4/2001 | Finarov et al. | 6,434,408 B1 | 8/2002 | Heckel et al. |
| 6,217,523 B1 | 4/2001 | Amano et al. | 6,438,396 B1 | 8/2002 | Cook |
| 6,222,189 B1 | 4/2001 | Misner et al. | 6,438,399 B1 | 8/2002 | Kurth |
| 6,223,064 B1 | 4/2001 | Lynn | 6,449,501 B1 | 9/2002 | Reuss |
| 6,226,539 B1 | 5/2001 | Potratz | 6,453,183 B1 | 9/2002 | Walker |
| 6,226,540 B1 | 5/2001 | Bernreuter et al. | 6,453,184 B1 | 9/2002 | Hyogo et al. |
| 6,229,856 B1 | 5/2001 | Diab et al. | 6,456,862 B2 | 9/2002 | Benni |
| 6,230,035 B1 | 5/2001 | Aoyagi et al. | 6,461,305 B1 | 10/2002 | Schnall |
| 6,233,470 B1 | 5/2001 | Tsuchiya | 6,463,310 B1 | 10/2002 | Swedlow et al. |
| 6,236,871 B1 | 5/2001 | Tsuchiya | 6,463,311 B1 | 10/2002 | Diab |
| 6,236,872 B1 | 5/2001 | Diab et al. | 6,466,808 B1 | 10/2002 | Chin et al. |
| 6,240,305 B1 | 5/2001 | Tsuchiya | 6,466,809 B1 | 10/2002 | Riley |
| 6,253,097 B1 | 6/2001 | Aronow et al. | 6,470,199 B1 | 10/2002 | Kopotic et al. |
| 6,253,098 B1 | 6/2001 | Walker et al. | 6,470,200 B2 | 10/2002 | Walker et al. |
| 6,256,523 B1 | 7/2001 | Diab et al. | 6,480,729 B2 | 11/2002 | Stone |
| 6,256,524 B1 | 7/2001 | Walker et al. | 6,490,466 B1 | 12/2002 | Fein et al. |
| 6,261,236 B1 | 7/2001 | Grimblatov | 6,493,568 B1 | 12/2002 | Bell |
| 6,263,221 B1 | 7/2001 | Chance et al. | 6,496,711 B1 | 12/2002 | Athan et al. |
| 6,263,222 B1 | 7/2001 | Diab et al. | 6,498,942 B1 | 12/2002 | Esenaliev et al. |
| 6,263,223 B1 | 7/2001 | Sheperd et al. | 6,501,974 B2 | 12/2002 | Huiku |
| 6,266,546 B1 | 7/2001 | Steuer et al. | 6,501,975 B2 | 12/2002 | Diab et al. |
| 6,266,547 B1 | 7/2001 | Walker et al. | 6,505,060 B1 | 1/2003 | Norris |
| 6,272,363 B1 | 8/2001 | Casciani et al. | 6,505,061 B2 | 1/2003 | Larson |
| 6,278,522 B1 | 8/2001 | Lepper, Jr. et al. | 6,505,133 B1 | 1/2003 | Hanna et al. |
| 6,280,213 B1 | 8/2001 | Tobler et al. | 6,510,329 B2 | 1/2003 | Heckel |
| 6,280,381 B1 | 8/2001 | Malin et al. | 6,510,331 B1 | 1/2003 | Williams et al. |
| 6,285,894 B1 | 9/2001 | Oppelt et al. | 6,512,937 B2 | 1/2003 | Blank et al. |
| 6,285,895 B1 | 9/2001 | Ristolainen et al. | 6,515,273 B2 | 2/2003 | Al-Ali |
| 6,285,896 B1 | 9/2001 | Tobler et al. | 6,519,484 B1 | 2/2003 | Lovejoy et al. |
| 6,298,252 B1 | 10/2001 | Kovach et al. | 6,519,486 B1 | 2/2003 | Edgar, Jr. et al. |
| 6,308,089 B1 | 10/2001 | Von der Ruhr et al. | 6,519,487 B1 | 2/2003 | Parker |
| 6,321,100 B1 | 11/2001 | Parker | 6,525,386 B1 | 2/2003 | Mills et al. |
| 6,330,468 B1 | 12/2001 | Scharf | 6,526,300 B1 | 2/2003 | Kiani et al. |
| 6,334,065 B1 | 12/2001 | Al-Ali et al. | 6,526,301 B2 | 2/2003 | Larsen et al. |
| 6,339,715 B1 | 1/2002 | Bahr et al. | 6,541,756 B2 | 4/2003 | Schulz et al. |
| 6,342,039 B1 | 1/2002 | Lynn | 6,542,764 B1 | 4/2003 | Al-Ali et al. |
| 6,343,223 B1 | 1/2002 | Chin et al. | 6,546,267 B1 | 4/2003 | Sugiura et al. |
| 6,343,224 B1 | 1/2002 | Parker | 6,553,241 B2 | 4/2003 | Mannheimer et al. |
| 6,349,228 B1 | 2/2002 | Kiani et al. | 6,553,242 B1 | 4/2003 | Sarussi |
| 6,351,658 B1 | 2/2002 | Middleman et al. | 6,553,243 B2 | 4/2003 | Gurley |
| 6,353,750 B1 | 3/2002 | Kimura | 6,554,788 B1 | 4/2003 | Hunley |
| 6,356,774 B1 | 3/2002 | Bernstein et al. | 6,556,852 B1 | 4/2003 | Schulze et al. |
| 6,360,113 B1 | 3/2002 | Dettling | 6,560,470 B1 | 5/2003 | Pologe |
| 6,360,114 B1 | 3/2002 | Diab et al. | 6,564,077 B2 | 5/2003 | Mortara |
| 6,361,501 B1 | 3/2002 | Amano et al. | 6,564,088 B1 | 5/2003 | Soller et al. |
| 6,363,269 B1 | 3/2002 | Hanna et al. | 6,571,113 B1 | 5/2003 | Fein et al. |
| D455,834 S | 4/2002 | Donars et al. | 6,571,114 B1 | 5/2003 | Koike et al. |
| 6,370,408 B1 | 4/2002 | Merchant et al. | 6,574,491 B2 | 6/2003 | Elghazzawi |
| 6,370,409 B1 | 4/2002 | Chung et al. | 6,580,086 B1 | 6/2003 | Schulz et al. |
| 6,371,921 B1 | 4/2002 | Caro | 6,584,336 B1 | 6/2003 | Ali et al. |
| 6,374,129 B1 | 4/2002 | Chin et al. | 6,587,703 B2 | 7/2003 | Cheng et al. |
| 6,377,829 B1 | 4/2002 | Al-Ali et al. | 6,587,704 B1 | 7/2003 | Fine et al. |
| 6,381,479 B1 | 4/2002 | Norris | 6,589,172 B2 | 7/2003 | Williams et al. |
| 6,381,480 B1 | 4/2002 | Stoddar et al. | 6,591,122 B2 | 7/2003 | Schmitt |
| 6,385,471 B1 | 5/2002 | Mortz | 6,591,123 B2 | 7/2003 | Fein et al. |
| 6,385,821 B1 | 5/2002 | Modgil et al. | 6,594,511 B2 | 7/2003 | Stone et al. |
| 6,388,240 B2 | 5/2002 | Schulz et al. | 6,594,512 B2 | 7/2003 | Huang |
| 6,393,310 B1 | 5/2002 | Kuenster | 6,594,513 B1 | 7/2003 | Jobsis et al. |

| | | |
|---|---|---|
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |

| Patent/Pub No. | Date | Inventor |
|---|---|---|
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,162,288 B2 | 1/2007 | Nordstrom et al. |
| 7,190,987 B2 | 3/2007 | Lindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,881 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,280,858 B2 | 10/2007 | Al-Ali et al. |
| 7,295,866 B2 | 11/2007 | Al-Ali |
| 7,305,262 B2 | 12/2007 | Brodnick et al. |
| 7,315,753 B2 | 1/2008 | Baker, Jr. et al. |
| 2002/0016537 A1 | 2/2002 | Muz et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0030230 A1 | 2/2004 | Norris |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2005/0004479 A1 | 1/2005 | Townsend et al. |
| 2005/0014999 A1 | 1/2005 | Rahe-Meyer |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0197548 A1 | 9/2005 | Dietiker |
| 2005/0228248 A1 | 10/2005 | Dietiker |
| 2005/0256386 A1 | 11/2005 | Chan |
| 2005/0272986 A1 | 12/2005 | Smith |
| 2005/0277819 A1 | 12/2005 | Kiani et al. |
| 2006/0020179 A1 | 1/2006 | Anderson |
| 2006/0030764 A1 | 2/2006 | Porges |
| 2006/0058594 A1 | 3/2006 | Ishizuka et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0155198 A1 | 7/2006 | Schmid |
| 2006/0173257 A1 | 8/2006 | Nagai |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073123 A1 | 3/2007 | Raridan |
| 2007/0073125 A1 | 3/2007 | Hoarau et al. |
| 2007/0073126 A1 | 3/2007 | Raridan |
| 2007/0073128 A1 | 3/2007 | Hoarau |
| 2007/0078315 A1 | 4/2007 | Kling et al. |
| 2007/0078316 A1 | 4/2007 | Hoarau |
| 2007/0260129 A1 | 11/2007 | Chin |
| 2007/0260130 A1 | 11/2007 | Chin |
| 2007/0260131 A1 | 11/2007 | Chin |
| 2007/0299328 A1 | 12/2007 | Chin et al. |

FOREIGN PATENT DOCUMENTS

| | | |
|---|---|---|
| DE | 3516338 | 11/1986 |
| DE | 37 03 458 | 8/1988 |
| DE | 3938759 | 5/1991 |
| DE | 4210102 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 | 9/1997 |

| | | | | | |
|---|---|---|---|---|---|
| DE | 19647877 | 4/1998 | JP | 8256996 | 10/1996 |
| DE | 10030862 | 1/2002 | JP | 9192120 | 7/1997 |
| DE | 20318882 | 4/2004 | JP | 10216113 | 8/1998 |
| EP | 0127947 | 5/1984 | JP | 10216114 | 8/1998 |
| EP | 00194105 | 9/1986 | JP | 10216115 | 8/1998 |
| EP | 00204459 | 12/1986 | JP | 10337282 | 12/1998 |
| EP | 0 262 779 | 4/1988 | JP | 11019074 | 1/1999 |
| EP | 0315040 | 10/1988 | JP | 11155841 | 6/1999 |
| EP | 0314331 | 5/1989 | JP | 11 188019 | 7/1999 |
| EP | 0 360 977 | 4/1990 | JP | 11244268 | 9/1999 |
| EP | 00430340 | 6/1991 | JP | 20107157 | 4/2000 |
| EP | 0435 500 | 7/1991 | JP | 20237170 | 9/2000 |
| EP | 0572684 | 5/1992 | JP | 21245871 | 9/2001 |
| EP | 00497021 | 8/1992 | JP | 22224088 | 8/2002 |
| EP | 0529412 | 8/1992 | JP | 22282242 | 10/2002 |
| EP | 0531631 | 9/1992 | JP | 23153881 | 5/2003 |
| EP | 0566354 | 4/1993 | JP | 23153882 | 5/2003 |
| EP | 0587009 | 8/1993 | JP | 23169791 | 6/2003 |
| EP | 00630203 | 9/1993 | JP | 23194714 | 7/2003 |
| EP | 0 572 684 | 12/1993 | JP | 23210438 | 7/2003 |
| EP | 00615723 | 9/1994 | JP | 23275192 | 9/2003 |
| EP | 00702931 | 3/1996 | JP | 23339678 | 12/2003 |
| EP | 00724860 | 8/1996 | JP | 24008572 | 1/2004 |
| EP | 00793942 | 9/1997 | JP | 24089546 | 3/2004 |
| EP | 0 864 293 | 9/1998 | JP | 24113353 | 4/2004 |
| EP | 01006863 | 10/1998 | JP | 24135854 | 5/2004 |
| EP | 01006864 | 10/1998 | JP | 24148069 | 5/2004 |
| EP | 0875199 | 11/1998 | JP | 24148070 | 5/2004 |
| EP | 00998214 | 12/1998 | JP | 24159810 | 6/2004 |
| EP | 0898933 | 3/1999 | JP | 24166775 | 6/2004 |
| EP | 01332713 | 8/2003 | JP | 24194908 | 7/2004 |
| EP | 01469773 | 8/2003 | JP | 24202190 | 7/2004 |
| EP | 1502529 | 7/2004 | JP | 24248819 | 9/2004 |
| EP | 01491135 | 12/2004 | JP | 24248820 | 9/2004 |
| FR | 2685865 | 1/1992 | JP | 24261364 | 9/2004 |
| GB | 2 259 545 | 3/1993 | JP | 24290412 | 10/2004 |
| JP | 63275325 | 11/1988 | JP | 24290544 | 10/2004 |
| JP | 2013450 | 1/1990 | JP | 24290545 | 10/2004 |
| JP | 2111343 | 4/1990 | JP | 24329406 | 11/2004 |
| JP | 02 191434 | 7/1990 | JP | 24329607 | 11/2004 |
| JP | 2237544 | 9/1990 | JP | 24329928 | 11/2004 |
| JP | 03 173536 | 7/1991 | JP | 24337605 | 12/2004 |
| JP | 3170866 | 7/1991 | JP | 24344367 | 12/2004 |
| JP | 3245042 | 10/1991 | JP | 24351107 | 12/2004 |
| JP | 4174648 | 6/1992 | JP | 25034472 | 2/2005 |
| JP | 4191642 | 7/1992 | WO | WO 89/09566 | 10/1989 |
| JP | 4332536 | 11/1992 | WO | WO 90/01293 | 2/1990 |
| JP | 3124073 | 3/1993 | WO | WO 90/04352 | 5/1990 |
| JP | 5049624 | 3/1993 | WO | WO 91/01678 | 2/1991 |
| JP | 5049625 | 3/1993 | WO | WO 91/11137 | 8/1991 |
| JP | 3115374 | 4/1993 | WO | WO 92/00513 | 1/1992 |
| JP | 2005/200031 | 8/1993 | WO | WO 92/21281 | 12/1992 |
| JP | 5212016 | 8/1993 | WO | WO 93/09711 | 5/1993 |
| JP | 06014906 | 1/1994 | WO | WO 93/13706 | 7/1993 |
| JP | 6016774 | 3/1994 | WO | WO 93/16629 | 9/1993 |
| JP | 3116255 | 4/1994 | WO | WO 94/03102 | 2/1994 |
| JP | 6029504 | 4/1994 | WO | WO 94/23643 | 10/1994 |
| JP | 6098881 | 4/1994 | WO | WO 95/02358 | 1/1995 |
| JP | 06 154177 | 6/1994 | WO | WO 95/12349 | 5/1995 |
| JP | 6269430 | 9/1994 | WO | WO 95/16970 | 6/1995 |
| JP | 6285048 | 10/1994 | WO | WO 96/13208 | 5/1996 |
| JP | 7001273 | 1/1995 | WO | WO 96/39927 | 12/1996 |
| JP | 7124138 | 5/1995 | WO | WO 97/36536 | 10/1997 |
| JP | 7136150 | 5/1995 | WO | WO 97/36538 | 10/1997 |
| JP | 3116259 | 6/1995 | WO | WO 97/49330 | 12/1997 |
| JP | 3116260 | 6/1995 | WO | WO 98/17174 | 4/1998 |
| JP | 7155311 | 6/1995 | WO | WO 98/18382 | 5/1998 |
| JP | 7155313 | 6/1995 | WO | WO 98/43071 | 10/1998 |
| JP | 3238813 | 7/1995 | WO | WO 98/51212 | 11/1998 |
| JP | 7171139 | 7/1995 | WO | WO 98/57577 | 12/1998 |
| JP | 3134144 | 9/1995 | WO | WO 99/00053 | 1/1999 |
| JP | 7236625 | 9/1995 | WO | WO 99/32030 | 7/1999 |
| JP | 7246191 | 9/1995 | WO | WO 99/47039 | 9/1999 |

| | | |
|---|---|---|
| WO | WO 99/63884 | 12/1999 |
| WO | WO 00/21438 | 4/2000 |
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 03/092490 A2 | 11/2003 |
| WO | WO 04/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |

OTHER PUBLICATIONS

U.S. Appl. No. 11/525,704, filed Sep. 22, 2006, Hoarau.
U.S. Appl. No. 11/525,693, filed Sep. 22, 2006, Hoarau.
U.S. Appl. No. 11/525,396, filed Sep. 22, 2006, Hoarau.
U.S. Appl. No. 11/525,635, filed Sep. 22, 2006, Hoarau.
U.S. Appl. No. 11/507,814, filed Aug. 22, 2006, Baker Jr. et al.
U.S. Appl. No. 11/527,762, filed Sep. 26, 2006, Ollerdessen.
Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).
Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).
Aoyagi, T., et al.; "Analysis of Motion Artifacts in Pulse Oximetry," *Japanese Society ME*, vol. 42, p. 20 (1993) (Article in Japanese—contains English summary of article).
Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).
Vincente, L.M., et al.; "Adaptive Pre-Processing of Photoplethysmographic Blood Volume Pulse Measurements," pp. 114-117 (1996).
Plummer, John L., et al.; "Identification of Movement Artifact by the Nellcor N-200 and N-3000 Pulse Oximeters," *Journal of clinical Monitoring*, vol. 13, pp. 109-113 (1997).
Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).
Poets, C. F., et al.; "Detection of movement artifact in recorded pulse oximeter saturation," *Eur. J. Pediatr.*; vol. 156, pp. 808-811 (1997).
Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximer signals when the usual probe cannot be used," *International journatl of clinical Monitoring and Computing*, vol. 14, pp. 23-28 (1997).
Nijland, Roel, et al.; "Validation of Reflectance Pulse Oximetry: An Evaluation of a new Sensor in Piglets," *Journal of Clinical Monitoring*, vol. 13, pp. 43-49 (1997).
Soto, Denise A.; "A Comparative Study of Pulse Oximeter Measurements: Digit Versus Earlobe," Master of Science Thesis, California State University Dominguez Hills, May 1997, 46 pgs.
Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).
Izumi, Akio, et al.; "Accuracy and Utility of a New Reflectance Pulse Oximeter for Fetal Monitoring During Labor," *Journal of Clinical Monitoring*, vol. 13, pp. 103-108 (1997).
Mannheimer, Paul, D., et al.; "Wavelength Selection for Low-Saturation Pulse Oximetry," *IEEE Transactions on Biomedical Engineering*, vol. 44, No. 3, pp. 148-158 (Mar. 1997).
"Smaller Product, Tighter Tolerances Pose Dispensing Challenges for Medical Device Manufacturer," *Adhesives Age*, pp. 40-41 (Oct. 1997).
Buschman, J.P., et al.; "Principles and Problems of Calibration of Fetal Oximeters," *Biomedizinische Technik*, vol. 42, pp. 265-266 (1997).
Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.
Leahy, Martin J., et al.; "Sensor Validation in Biomedical Applications," *IFAC Modelling and Control in Biomedical Systems*, Warwick, UK; pp. 221-226 (1997).
Barreto, Armando B., et al.; "Adaptive LMS Delay Measurement in dual Blood Volume Pulse Signals for Non-Invasive Monitoring," *IEEE*, pp. 117-120 (1997).
Crilly, Paul B., et al.; "An Integratd Pulse Oximeter System for Telemedicine Applications," *IEEE Instrumentation and Measurement Technology Conference*, Ottawa, Canada; May 19-21, 1997; pp. 102-104.
DeKock, Marc; "Pulse Oximetry Probe Adhesive Disks: a Potential for Infant Aspiration," *Anesthesiology*, vol. 89, pp. 1603-1604 (1998).
East, Christine E., et al.; "Fetal Oxygen Saturation and Uterine Contractions During Labor," *American Journal of Perinatology*, vol. 15, No. 6, pp. 345-349 (Jun. 1998).
Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).
Yang, Boo-Ho, et al.; "A Twnety-Four Hour Tele-Nursing System Using a Ring Sensor," *Proceedings of the 1998 IEEE International Conference on Robotics & Automation*, Leaven, Belgium, May 1998; pp. 387-392.
König, Volker, et al.; "Reflectance Pulse Oximetry—Principles and Obstetric Application in the Zurich System," *Journal of Clinical Monitoring and Computing*, vol. 14, pp. 403-412 (1998).
Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).
Hayes, Matthew J., et al.; "Quantitative evaluation of photoplethysmographic artifact reduction for pulse oximetry," *SPIE*, vol. 3570, pp. 138-147 (Sep. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Reistant, Power-Efficient Design of Finger-Ring Plethysomographic Sensor—Part I: Design and Anlaysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vincenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Repiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximer for Pre-hospital Evaluation," *Journal of the Japanse Society of Emergency Medicine*, Kanto Region, vol. 21, pp. 26-27 (2000) (Article in Japanse—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recording using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescence Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisy Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains Englsih summary of article).

Nakagawa, M., et al.; "Oxygen Saturation Monitor," *Neonatal Monitoring*, vol. 26, No. 5, pp. 536-539 (2003) (Article Japanese—contains English summary of article).

Kubota, H., et al.; "Simultaneous Monitoring of PtcCO2 and SpO2 using a Miniature earlobe sensor," *Jinko Kokyo (Artificial Respiration)*, vol. 20, No. 1, pp. 24-29 (2003).

Lebak, J.W., et al.; "Implementation of a Standards-Based Pulse Oximeter on a Wearable, Embedded Platform," *Proceedings of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceedings of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings of the 26th Annual International conference o the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference on the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmut-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103, undated.

J. Huang, et al.; "Low Power Motion Tolerant Pulse Oximetry," *Abstracts*, A7, p. S103, undated.

P. Lang, et al.; "Signal Identification and Quality Indicator™ for Motion Resistant Pulse Oximetry," *Abstracts*, A10, p. S105, undated.

Hamilton, Patrick S., et al.; "Effect of Adaptive Motion-Artifact Reduction on QRS Detection," *Biomedical Instrumentation & Technology*, pp. 197-202, undated.

Kim, J.M., et al.; "Signal Processing Using Fourier & Wavelet Transform," pp. II-310-II-311, undated.

Lee, C.M., et al.; "Reduction of Motion Artifacts from Photoplethysmographic Records Using a Wavelet Denoising Approach," *IEEE*, pp. 194-195, undated.

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87, undated.

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

TECHNIQUES FOR DETECTING HEART PULSES AND REDUCING POWER CONSUMPTION IN SENSORS

CROSS-REFERENCE TO RELATED APPLICATIONS

This application is a continuation of application Ser. No. 10/787,851, filed Feb. 25, 2004, now U.S. Pat. No. 7,162,288.

BACKGROUND OF THE INVENTION

The present invention relates to techniques for detecting heart pulses and reducing power consumption in sensors and oximeter systems, and more particularly, to techniques for distinguishing heart pulses in a sensor signal from noise and adjusting drive current provided to light emitting elements in response to a signal-to-noise ratio of the pulse in order to reduce power consumption.

Pulse oximetry is a technology that is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient.

Measurement of these characteristics has been accomplished by use of a non-invasive sensor. The sensor has a light source such as a light emitting diode (LED) that scatters light through a portion of the patient's tissue where blood perfuses the tissue. The sensor also has a photodetector that photoelectrically senses the absorption of light at various wavelengths in the tissue. The photodetector generates a pulse oximeter signal that indicates the amount of light absorbed by the blood. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption.

For measuring blood oxygen level, oximeter sensors typically have a light source that is adapted to generate light of at least two different wavelengths, and with photodetectors sensitive to these wavelengths, in accordance with known techniques for measuring blood oxygen saturation. A typical pulse oximeter will alternately illuminate the patient with red and infrared light using two LEDs to obtain two different detector signals.

The pulse oximeter signal generated by the photodetector usually contains components of noise introduced by the electronics of the oximeter, by the patient, and by the environment. Noisy signals have a low signal-to-noise ratio. A pulse oximeter cannot accurately identify the blood oxygen saturation when the signal-to-noise ratio of the pulse oximeter signal is too low.

To improve the signal-to-noise ratio of the pulse oximeter signal, a pulse oximeter system will typically drive the LEDs with a large amount of current. A servo in the pulse oximeter will typically drive as much current as possible through the LEDs without causing the oximeter to be over-ranged (i.e., driven to full rail). The large drive current causes the LEDs to generate more light and to consume more power. Because the photodetector is able to sense more of the light from the LEDs, the signal-to-noise ratio of the pulse oximeter signal is higher.

Increasing the drive current of the LEDs to improve the signal-to-noise ratio of the pulse oximeter signal causes the system to consume an undesirably large amount of power. The large amount of power consumption can be a problem for oximeter systems that are battery operated.

It would therefore be desirable to provide pulse oximeter systems that consume less power without negatively compromising the signal-to-noise ratio of the pulse oximeter signal.

BRIEF SUMMARY OF THE INVENTION

The present invention provides CPU cycle efficient techniques for sensing heart pulses in a signal from a sensor. The sensor signal can be, for example, a pulse oximeter signal generated by a photodetector in a pulse oximeter sensor. The signal component of the sensor signal is measured by identifying potential systolic transitions of the cardiac cycle. The systolic transitions are detected using a derivative averaging scheme. The moving minimum and the moving maximum of the average derivative are compared to a scaled sum of the minimum and maximum to identify the systolic transitions. The systolic transitions correspond to a signal component of the sensor signal. The signal component is compared to a noise component to determine the signal-to-noise ratio of the signal.

The present invention also provides techniques for reducing power consumption in a sensor. After the signal-to-noise ratio of the pulse oximeter has been determined, the signal-to-noise ratio is compared to a threshold. In response to the output of the comparison, the drive current of light emitting elements in the sensor is dynamically adjusted to reduce power consumption and to maintain the signal-to-noise ratio at an adequate level for signal processing.

The present invention also provides techniques for sensing and adjusting the gain of a transimpedance amplifier to reduce the effect of ambient noise in a sensor. A gain control feedback loop senses the magnitude of the sensor signal when the light emitting elements are off. The gain control loop can include this information to effectively control the gain of the transimpedance amplifier.

For a further understanding of the nature and advantages of the invention, reference should be made to the following description taken in conjunction with the accompanying drawings.

DETAILED DESCRIPTION OF THE INVENTION

Figure 1:
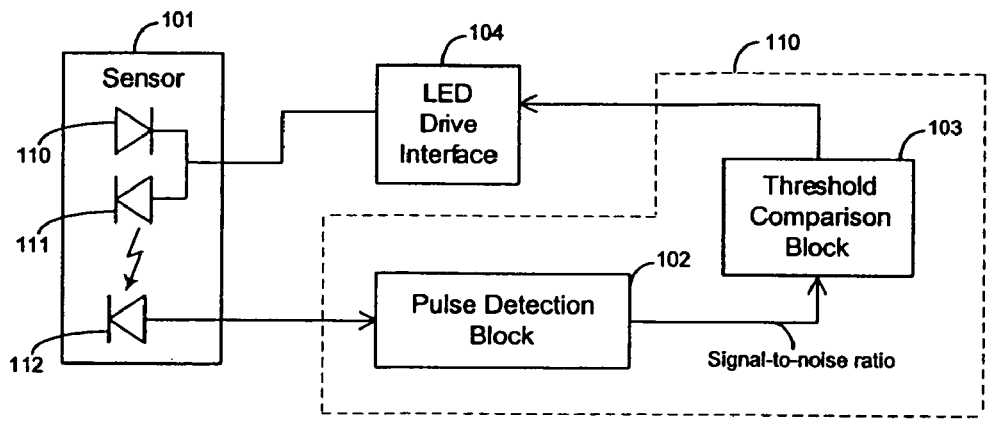
FIG. 1 illustrates a block diagram of a pulse oximeter system with reduced power consumption according to an embodiment of the present invention.

The techniques of the present invention can be used in the context of a pulse oximeter system. A pulse oximeter system receives a pulse oximeter signal from a photodetector in a pulse oximeter sensor. FIG. 1 illustrates a block diagram of pulse oximeter system according to an embodiment of the present invention. The pulse oximeter system includes an oximeter sensor 101.

An oximeter sensor of the present invention can utilize any suitable number of light emitting elements. For example, a sensor of the present invention can have 1, 2, 3, or 4 light emitting elements. In the example of FIG. 1, sensor 101 has two LEDs 110 and 111 that emit two different wavelengths of light.

Sensor 101 also includes photodetector 112 that senses light from LEDs 110 and 111 after the light has passed through the patient's tissue. The pulse oximeter system also includes feedback loop circuitry 110 and LED drive interface 104. Feedback loop circuitry 110 includes pulse detection block 102 and threshold comparison block 103.

Photodetector 112 transmits the pulse oximeter signal to pulse detection block 102. Pulse detection block 102 has a servo that measures the signal component of the pulse oximeter signal by identifying the systolic transitions. The pulse detection block 102 and the threshold comparison block 103 form a feedback loop 110 around the sensor to control the drive current of the LEDs and the signal-to-noise ratio of the pulse oximeter signal, as will be discussed in detail below.

A cardiac pulse can be divided into a diastolic and systolic period. The systolic period is typically characterized by a rapid change in value due to the contraction of the heart. The diastolic period is typically characterized by a gradual change in value, due to the relaxation and refilling of the heart chambers.

Systolic transitions in the pulse oximeter signal are detected using a three step maximum and minimum derivative averaging scheme, which is discussed in further detail below. Qualification routines are then used to filter out false positives. The resulting data contains the systolic transitions separated from the non-systolic periods in the pulse oximeter signal.

Pulse detection block 102 then compares the amplitude of the systolic portion of the pulse oximeter signal to a noise component to generate a value for the signal-to-noise ratio of the pulse oximeter signal. Subsequently, threshold comparison block 103 compares this signal-to-noise ratio to a threshold level to determine whether the signal-to-noise ratio is high enough such that the pulse oximeter signal can be used to accurately calculate pulse rate and oxygen saturation. Too much noise obscures the pulse rate and oxygen saturation information in the signal. Noise can degrade the signal to the point that it cannot be used to accurately calculate pulse rate or oxygen saturation.

Threshold comparison block 103 preferably contains two hysteretic threshold levels. In this embodiment, threshold comparison block 103 senses whether the signal-to-noise ratio is greater than a maximum threshold level or less than a minimum threshold level. As an example, the maximum threshold level can represent a signal-to-noise ratio of 128:1, and the minimum threshold level can represent a signal-to-noise ratio of 8:1. These are merely two examples of thresholds levels. They are not intended to limit the scope of the present invention. Prior art oximeter systems, for example, operate at a signal-to-noise ratio of 10,000:1 or higher, because they drive the LEDs as bright as possible.

If the signal-to-noise ratio is greater than the maximum threshold level, threshold comparison block 103 sends a signal to LED drive interface 104 to reduce the LED current. Based on the value of the signal-to-noise ratio, threshold comparison block 103 can determine how much the LED drive current needs to be reduced to decrease the signal-to-noise ratio while maintaining the signal level within the minimum and maximum threshold levels. LED drive interface 104 responds by decreasing the LED drive current to the value indicated by threshold comparison block 103.

The feedback loop continuously monitors the signal-to-noise ratio of the pulse oximeter signal and dynamically adjusts the LED drive current and subsequent system gain until the signal-to-noise ratio is less than the maximum threshold. The oximeter system saves power by substantially reducing the LED drive current (relative to prior art systems), while maintaining the signal-to-noise ratio of the pulse oximeter signal within an acceptable range.

The signal-to-noise ratio can also drop too low for a number of reasons. For example, the noise in the pulse oximeter may increase, or the strength of the signal component may decrease if the blood oxygen saturation of the patient decreases. In any event, the system of FIG. 1 senses when the magnitude of the pulse oximeter signal is too low and increases the LED drive current accordingly.

If the signal-to-noise ratio is less than the minimum threshold level, threshold comparison block 103 sends a signal to LED drive interface 104 to increase the LED current. Based on the value of the signal-to-noise ratio, the threshold comparison can determine how much the LED drive current needs to be increased to increase the signal-to-noise ratio while maintaining the signal within the minimum and maximum threshold levels. LED drive interface 104 responds by increasing the LED drive current to the value indicated by the threshold comparison system.

The feedback loop continuously monitors the signal-to-noise ratio of the pulse oximeter signal and dynamically adjusts the LED drive current until the signal-to-noise ratio is greater than the minimum threshold level. The minimum threshold indicates a minimum allowable value for the signal-to-noise ratio for which the pulse rate and the oxygen saturation can be accurately calculated.

If the signal-to-noise ratio falls between the maximum and minimum threshold levels, the oximeter system maintains the LED drive current at a stable value. The oximeter system maintains equilibrium until the signal-to-noise ratio of the pulse oximeter signal moves outside the range of the thresholds. Thus, an oximeter system of the present invention contains a dynamic feedback loop as shown in FIG. 1. The dynamic feedback loop automatically adjusts the drive current of the LEDs to reduce power consumption in the sensor and to maintain the signal-to-noise ratio at an acceptable level for the purpose of accurately calculating blood oxygen saturation levels.

According to a preferred embodiment of the present invention, the hardware for the servo in pulse detection block 102 maintains a predictable relationship between the power that LED drive 104 attempts to the drive the LEDs at and the radiated output power actually generated by the LEDs. By providing a predictable relationship between the input and output power, the feedback loop is more likely to acquire the oxygen saturation from the pulse oximeter signal in significantly less time, requiring less executions of the servo.

As the gain of the pulse oximeter signal is increased, the signal component generally increases faster than the noise component (at least to a point below the highest gain settings). The effect that increasing the gain of the pulse oximeter signal has on the signal-to-noise ratio in a particular system should be understood. Certain combinations of gain may cause more noise to be present in the pulse oximeter signal. Therefore, the gain stages in the pulse detection block preferably take advantage of characteristics of the gain-to-noise variability.

For example, the signal from the photodetector that is sampled using an analog-to-digital converter is fed into a gain block. The gain block includes several gain stages to achieve a known response. The noise is measured at each of the gain stages, and then stored for later use to calculate the signal-to-noise ratio.

Techniques for identifying the systolic portions of a pulse oximeter signal generated by an oximeter sensor are now discussed. The systole identification of the present invention uses a three step maximum and minimum derivative averaging scheme in order to detect cardiac systolic events.

Figure 2:
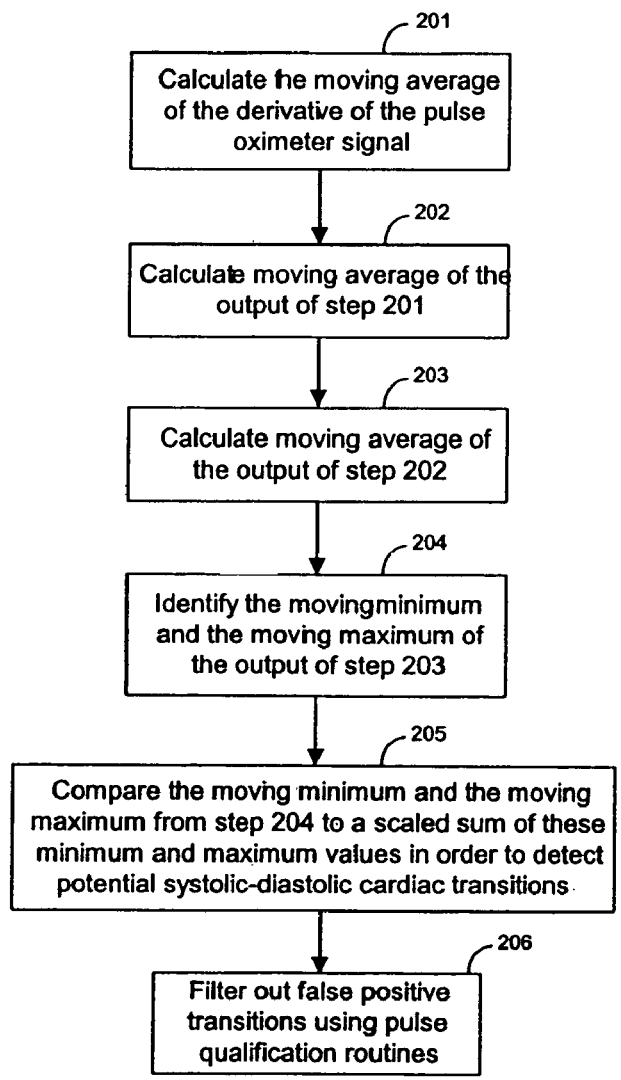
FIG. 2 is a flow chart that illustrates a process for identifying the systolic period of a pulse oximeter signal according to an embodiment of the present invention.

FIG. 2 illustrates one method for identifying the systolic period of a pulse oximeter signal. In the first step 201, the moving average of the derivative of the pulse oximeter signal is found. In the second step 202, the moving average of the output of the first step 201 is found. In the third step 203, the moving average of the output of the second step 202 is found.

Next, the moving maximum and the moving minimum of the output of the third step is found at step 204. At step 205, systole transitions are detected by comparing this moving minimum and moving maximum to a scaled sum of the moving minimum and maximum. For example, the scaled sum of the moving minimum and maximum values can be a fractional sum of the minimum and maximum moving averages.

When the minimum output of step 204 becomes less than a fractional sum of the maximum and minimum moving averages, the system determines that the pulse oximeter signal is entering systole. When the minimum output of step 204 becomes more than a fractional sum of the maximum and minimum moving averages, the system determines that pulse oximeter signal is exiting systole.

The two predetermined fractional sums can be selected to be any suitable values. As a specific example, the system can determine that the pulse oximeter signal is entering systole when the minimum derivative output becomes less than $\frac{1}{16}$ the sum of the minimum and maximum moving averages of the third stage. As another example, the system can determine that the pulse oximeter signal is exiting systole when the minimum derivative output becomes more than $\frac{1}{8}$ the sum of the maximum and minimum moving averages of the third stage. These two examples are not intended to limit the scope of the present invention. Many other fractional values can also be used to identify systole transitions.

These techniques of the present invention can detect and qualify pulses using CPU, RAM, and ROM efficient algorithms. Minimal processor resources are required to perform oximetry calculations with a comparable level of saturation and pulse rate performance as prior art oximeter technology.

Figure 3A:
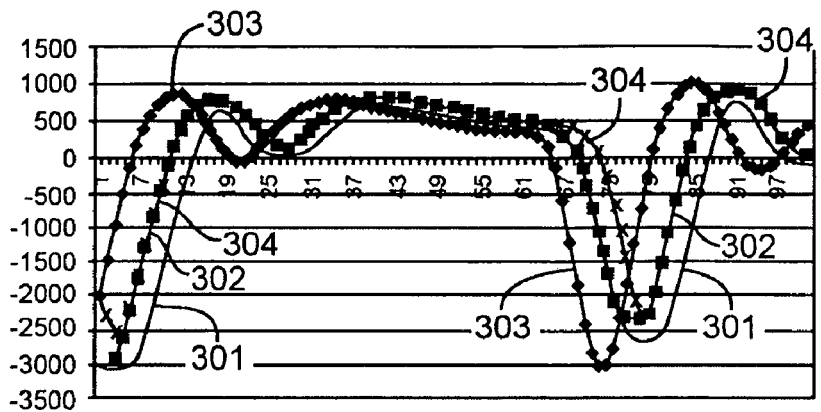
FIGS. 3A-3C are graphs that illustrates how systolic transitions are identified in pulse oximeter signals according to embodiments of the present invention.

Example waveforms for the results of these calculations are shown in FIG. 3A. Waveform 303 is an example of the derivative of a pulse oximeter signal. Waveforms 301 and 304 are examples of the minimum and maximum moving average of the pulse oximeter signal, respectively. Waveform 302 is an example of the output signal of the three-step moving average.

The output of the moving average is a smoothed and delayed version of the derivative of the pulse oximeter signal. The minimum output tracks the negative-going trends and lags the positive-going trends. The maximum output tracks the positive-going trends and lags the negative-going trends. These relationships are key to detecting potential systolic cardiac periods.

Figure 3B:
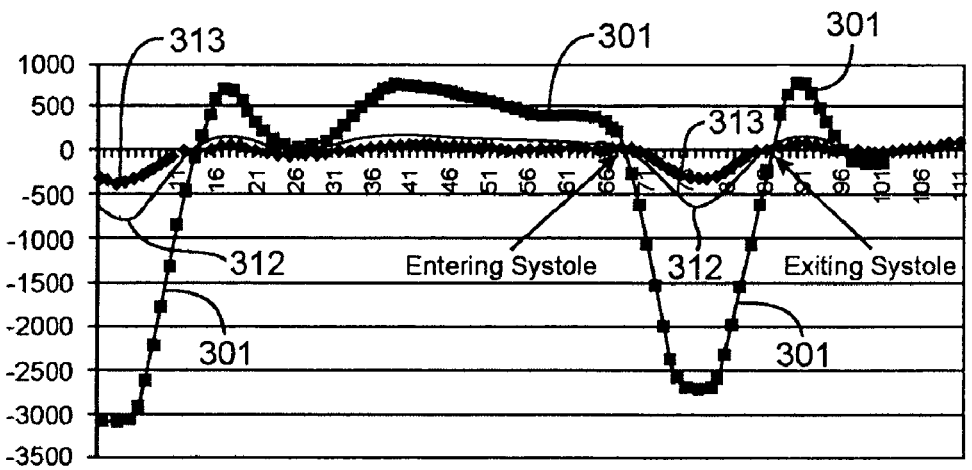

FIG. 3B shows examples of the minimum moving average 301 with a waveform 313 that represents $\frac{1}{16}$ of the sum of the minimum and maximum moving averages of the third stage. FIG. 3B also shows an example of waveform 312 that represents $\frac{1}{8}$ of the sum of the minimum and maximum moving averages of the third stage.

According to one embodiment of the present invention, waveforms 312 and 313 are compared to the minimum moving average waveform 301 at step 205 to identify the systolic period of the pulse oximeter signal. Alternatively, other scaled sums for the minimum and/or maximum moving averages can be used to identify systolic periods in the pulse oximeter signal. The beginning and the end of a systole in signal 301 are identified in FIG. 3B. The period between crossing points of signal 301 and signals 312/313 defines the systolic period.

Figure 3C:
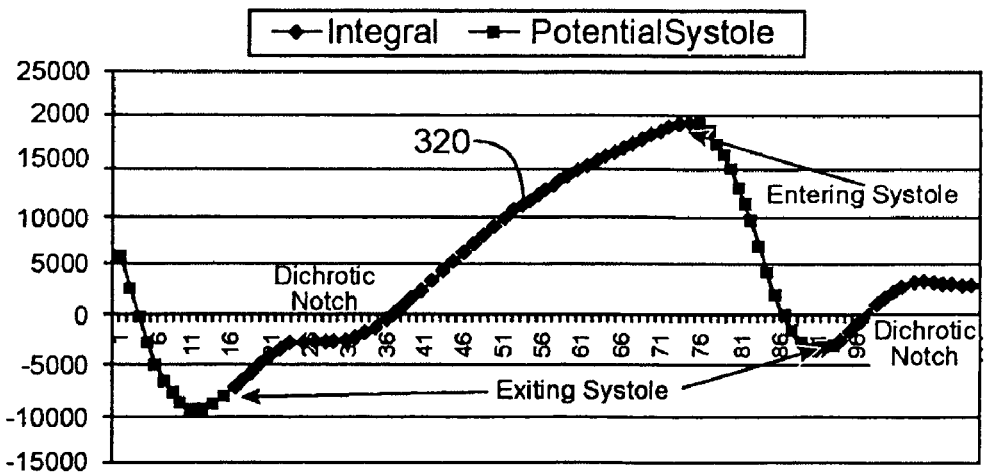

When applied to the original pulse oximeter signal 320, the systolic period identification is shown in FIG. 3C. The systolic period includes the time between the peak (i.e. maximum value) and the subsequent valley (i.e. minimum value) of pulse oximeter signal 320. The actual systolic period is identified in FIG. 3C as well as the dichrotic notch of the next pulse.

After the systolic period has been identified, unique pulse qualification tests based upon typical physiological pulse characteristics are applied to the systole pulse at step 206. The full pulse qualification tests remove false positive systolic detections (e.g., the dichrotic notch) and pulses that have an inadequate signal-to-noise ratio. False positives are portions of the signal that are falsely identified as systolic transitions in step 205. Pulse qualifications are used in step 206 to filter out false positives identified in step 205. The steps of FIG. 2 can be implemented in software or hardware.

Pulse qualification tests qualify cardiac pulses in the pulse oximeter signal. The pulse qualification tests are designed to identify cardiac pulses that have adequate signal-to-noise ratio for use in measuring pulse rate and blood oxygen saturation. The pulse qualification tests can include any number techniques including traditional pulse qualification techniques.

Some examples of pulse qualification tests according to particular embodiments of the present invention are now discussed. The qualifications are comparisons of special pulse characteristics to determined threshold values. For example, the pulse qualifications compare systolic area, width, and number of sub-peaks to fixed thresholds. Diastolic area, width, and number of sub-peaks are compared to thresholds. Systolic area and width are compared to diastolic area and width. Pulse area and width are compared to thresholds. All of the above individually are compared to the last N pulses detected.

Pulses that pass these qualifications can be used to measure pulse rate. To qualify the systolic periods for oxygen saturation calculations, the following additional qualifications are used. The lag/lead time between the infrared and red pulse detection are compared. The pulse size is compared to the N pulses qualified. The statistically significant coefficient of the best-fit line plot of the moving average between the infrared and the red signals is compared to fixed thresholds. The saturation rate-of-change is compared to fixed thresholds. Pulses that pass these additional qualifications can be used to measure oxygen saturation.

After the pulse qualification tests have filtered out false positives, the systolic periods are identified. The systolic periods represent a signal component of the pulse oximeter signal. The signal-to-noise ratio of the pulse oximeter signal is calculated by comparing the strength of the systolic period to the noise component of the pulse oximeter signal.

According to one embodiment, the noise component of a pulse oximeter sensor is calculated in advance using a separate instrument that measures noise in the pulse oximeter signal at various gain values. The measured noise component is then stored in memory for later use. The stored noise component is subsequently compared to the size of the systolic pulse for a particular gain value to determine the signal-to-noise ratio of the pulse oximeter signal.

According to another embodiment, dynamic measurements of the noise of the pulse oximeter system are made. These noise measurements can include electrical noise, ambient noise caused by ambient light, and/or noise (e.g. motion) caused by the patient. The dynamic noise measurement is updated continuously throughout the operation of the pulse oximeter sensor. An updated noise component is continuously compared to the pulse to calculate a more accurate signal-to-noise ratio of the pulse oximeter signal.

Once the signal-to-noise ratio of the pulse oximeter signal has been calculated, a determination is made as whether the signal-to-noise ratio falls within an acceptable range. The acceptable range is selected based on the relative noise component for accurately calculating oxygen saturation and pulse rate. If the ratio is outside the acceptable range, the feedback loop discussed above with respect to FIG. 1 adjusts the LED drive current to bring the signal-to-noise ratio within the acceptable range.

The present invention has the advantage of requiring fewer servo executions to acquire and maintain the oxygen saturation of the signal than many prior art techniques, particularly in the presence of patient motion interference. In many prior art oximeter systems, the LEDs are driven with a large current, and the pulse oximeter signal fills up its entire system dynamic range. The oximeter signal exceeds the system's current dynamic range as soon as the patient starts moving, and the signal is effectively lost (i.e., flat-line, invalid signal). Additional servo executions are required to re-acquire the signal. While the servo is executing, the sensor signal is not available; therefore, the oximeter cannot calculate pulse rate or oxygen saturation data from the pulse oximeter signal.

On the other hand, the LED drive current is substantially reduced in the present invention. The dynamic range is greatly increased relative to the size of the pulse oximeter signal, because the signal has been greatly reduced by cutting back on the LED drive current. The oximeter signal can now move around more within the dynamic range without requiring additional servo executions or changes to the LED settings. In the present invention, the patient can move around vigorously without causing the servo to execute in an attempt to re-acquire the signal. The techniques of the present invention can allow an oximeter system to be much more tolerant of patient motion.

Figure 4:
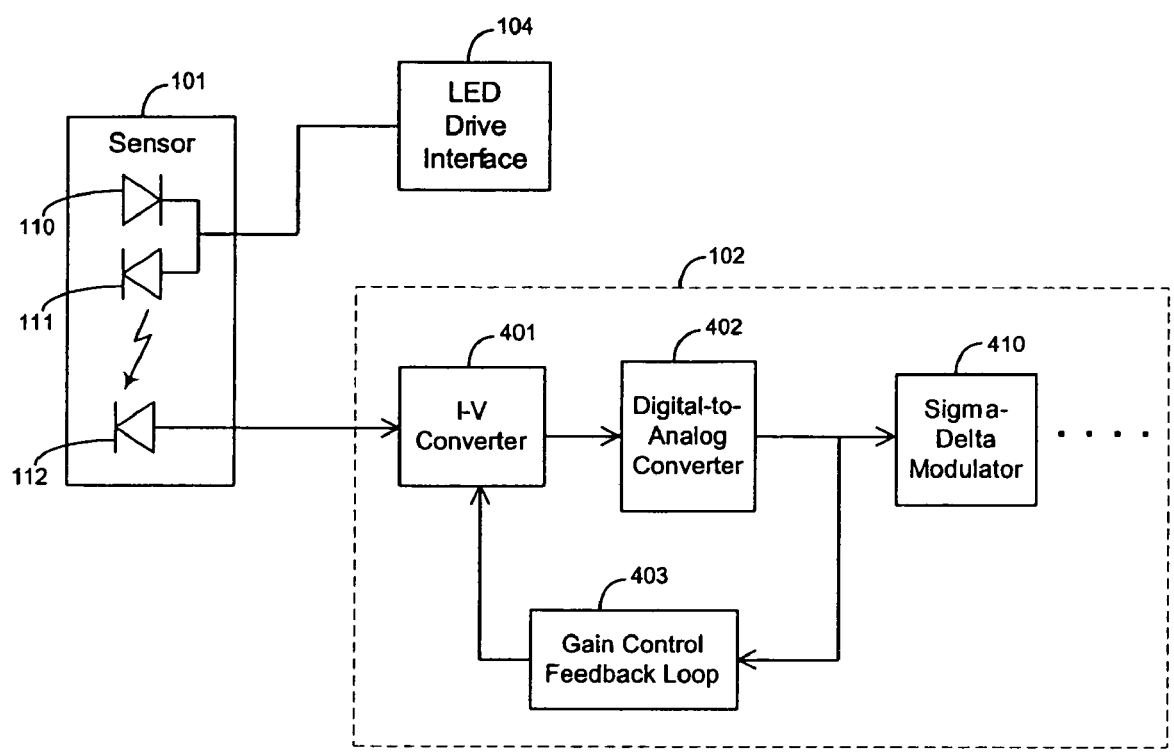
FIG. 4 illustrates a portion of a pulse oximeter system with a transimpedance amplifier, a sigma-delta modulator, an analog-to-digital converter, and a gain control feedback loop according to an embodiment of the present invention.

Pulse detection block 102 can include a transimpedance (I-V) amplifier or converter 401 that converts a current signal from photodetector 112 to a voltage signal as shown in FIG. 4. Ambient light in the environment adds a component of DC bias into the pulse oximeter signal. This DC bias shifts the pulse oximeter signal higher, closer to the rail of the dynamic range of the transimpedance amplifier.

According to an embodiment of the present invention, an analog-to-digital (A-to-D) converter 402 samples the output signal of transimpedance amplifier 401 during a time when either LED 110-111 is on or off to provide a continuous, real-time measurement of the ambient light and or noise that gets into sensor 101. This feature can also be used to provide information on the magnitude of the signal at the output of A-to-D converter 402.

The information about the signal magnitude from A-to-D converter 402 is fed back through gain control feedback loop 403 and used to choose an appropriate gain for transimpedance amplifier 401. For example, gain control feedback loop 403 causes the transimpedance gain of transimpedance amplifier 401 to increase or decrease to reduce and/or accommodate the effect of the environmental DC bias on the signal. This real-time measurement can also be used for determining a sensor-off condition, measuring electrical and optical noise, detecting transients in the signal, and detecting patient motion.

During the normal operation of the sensor, the LEDs can be pulsed on and off in any desired manner to provide the continuous (multiplexed), real-time measurement of the ambient light and other noise sources. For example, one red and one infrared LED can be alternately turned on and off in the following manner: red LED on and infrared LED off, then red LED off and infrared LED on, then both LEDs off, then red LED on and infrared LED off, etc, repeating in this sequence. As another example, one red and one infrared LED can be alternately turned on and off as follows: red LED on and infrared LED off, then both LEDs off, then red LED off and infrared LED on, then both LEDs off, then red LED on and infrared LED off, etc. repeating in this sequence. These patterns are examples that are not intended to limit the scope of the present invention.

Sigma-delta modulator 410 also receives the output signal of the transimpedance amplifier 402. Modulator 410 demodulates the signal from the photodetector into separate red and infrared components. The demodulation function can be performed in the digital domain using a software or firmware program run by a microcontroller. Further details of a Multi-Bit ADC With Sigma-Delta Modulation are discussed in commonly assigned, co-pending U.S. Patent Application 2005/0184895, to Ethan Petersen et al., filed concurrently herewith, which is incorporated by reference herein.

As will be understood by those of skill in the art, the present invention could be embodied in other specific forms without departing from the essential characteristic thereof. Accordingly, the foregoing description is intended to be illustrative, but not limiting, on the scope of the invention which is set forth in the following claims.

For example, the components in pulse detection block 102 that are shown in FIG. 4 can be implemented in systems other than pulse oximeter systems. These components can reduce the effect of noise in signals from other types of sensors as well.

What is claimed is:
1. A pulse oximeter system comprising:
a drive interface that controls drive current of light emitting elements in a pulse oximeter sensor; and
a feedback loop coupled around the pulse oximeter sensor and the drive interface that is capable of dynamically adjusting the drive current of the light emitting elements based at least in part upon results of a comparison between a signal-to-noise ratio of a pulse oximeter signal and a threshold, wherein the feedback loop is capable of detecting systolic transitions based at least in part upon a multi-step averaging scheme,
wherein the pulse oximeter signal is generated by a photodetector in the pulse oximeter sensor.
2. The pulse oximeter system as defined in claim 1 wherein the feedback loop causes the drive current of the light emitting elements to decrease if the signal-to-noise ratio of the pulse oximeter signal is greater than a maximum threshold, and the feedback loop causes the drive current of the light emitting elements to increase if the signal-to-noise ratio of the pulse oximeter signal is less than a minimum threshold.
3. The pulse oximeter system as defined in claim 1 wherein the feedback loop further comprises:
a pulse detection block that is capable of calculating the signal-to-noise ratio of the pulse oximeter signal; and a comparator that is capable of performing the comparison of the signal-to-noise ratio of the pulse oximeter signal to the threshold.

4. A method for reducing power consumption in a pulse oximeter sensor, the method comprising:
providing drive current to light emitting elements in the pulse oximeter sensor; and
dynamically determining a signal-to-noise ratio of a pulse oximeter signal generated by a photodetector in the pulse oximeter sensor, wherein determining the signal-to-noise ratio comprises measuring and storing the noise at each of a plurality of gain stages; and
dynamically adjusting the drive current of the light emitting elements based at least in part upon results of a comparison between the signal-to-noise ratio of the pulse oximeter signal and a threshold.

5. The method as defined in claim 4 wherein dynamically adjusting the drive current of the light emitting elements further comprises:
increasing the drive current provided to the light emitting elements if the signal-to-noise ratio of the pulse oximeter signal is less than a minimum threshold; and
decreasing the drive current provided to the light emitting elements if the signal-to-noise ratio of the pulse oximeter signal is greater than a maximum threshold.

6. A system coupled to a sensor, the system comprising:
a transimpedance amplifier capable of receiving a current signal from the sensor and converting the current signal to a voltage signal based at least in part upon a transimpedance gain;
an analog-to-digital converter capable of converting the voltage signal into a digital signal; and
a feedback loop capable of providing a feedback signal indicating a magnitude of the voltage signal from the transimpedance amplifier when light emitting elements in the sensor are on or off,
wherein the transimpedance gain is capable of being adjusted in response to the feedback signal to reduce the environmental DC bias on the voltage signal.

7. The system as defined in claim 6 wherein the sensor is a pulse oximeter sensor containing a photodetector.

8. The system as defined in claim 6 further comprising:
a pulse detector that is capable of calculating the signal-to-noise ratio of the signal from the sensor;
a comparator that is capable of comparing the signal-to-noise ratio to a threshold; and
a drive interface that is capable of controlling drive current of the light emitting elements.

9. A method for controlling drive current of light emitting elements in a pulse oximeter sensor, comprising:
using a pulse oximeter:
measuring a noise component of a pulse oximeter signal;
identifying a systolic period of the pulse oximeter signal;
performing first pulse qualification tests to qualify a systolic period for pulse rate measurement;
performing second pulse qualification tests to qualify the systolic period for oxygen saturation calculations, if the systolic period is qualified for pulse rate measurement;
determining a strength of the systolic period if the systolic period is qualified for oxygen saturation calculations;
identifying a signal-to-noise ratio by comparing the strength of the systolic period to the noise component; and
controlling the drive current based at least in part upon a comparison of the signal-to-noise ratio to a threshold.

10. The method of claim 9, comprising measuring the noise component before determining the strength of the systolic period and storing the measured noise component in memory for comparison with the strength of the systolic period.

11. The method of claim 9, comprising measuring the noise in the pulse oximeter signal at various gain values.

12. The method of claim 9, wherein the threshold comprises a maximum signal-to-noise ratio value of 128:1.

13. The method of claim 9, wherein the threshold comprises a minimum signal-to-noise ratio value of 8:1.

14. The method of claim 9, comprising calculating a series of moving averages based at least in part upon a derivative of the pulse oximeter signal to identify the systolic period.

15. The method of claim 14, comprising identifying a moving minimum and moving maximum of a last moving average of the series of moving averages to identify the systolic period.

16. The method of claim 9, comprising calculating a moving average of a derivative of the pulse oximeter signal to generate a first output, calculating a moving average of the first output to generate a second output, calculating a moving average of the second output to generate a third output, and identifying a moving minimum and a moving maximum of the third output to identify the systolic period.

17. The method of claim 16, comprising comparing the moving minimum and the moving maximum to a scaled sum of the moving minimum and the moving maximum to determine the systolic period.

18. A monitor for controlling drive current of light emitting elements in a pulse oximeter sensor, comprising:
an identification module capable of identifying a systolic period of a pulse oximeter signal;
a qualification module capable of performing multiple stages of pulse qualification tests to qualify the systolic period for oxygen saturation calculations;
a strength determination module capable of determining a strength of the systolic period if the systolic period is qualified for oxygen saturation calculations;
a ratio module capable of identifying a signal-to-noise ratio by comparing the strength of the systolic period to a measured value of a noise component of the pulse oximeter signal stored in a memory; and
a controller capable of controlling the drive current based at least in part upon a comparison of the signal-to-noise ratio to a threshold.

19. The monitor of claim 18, comprising a measurement module capable of measuring the noise component.

20. The monitor of claim 19, wherein the measurement module is capable of measuring the noise component at various gain values.

21. The monitor of claim 18, wherein the threshold comprises a maximum signal-to-noise ratio value of 128:1.

22. The monitor of claim 18, wherein the threshold comprises a minimum signal-to-noise ratio value of 8:1.

23. The monitor of claim 18, comprising a calculation module capable of calculating a series of moving averages based at least in part upon a derivative of the pulse oximeter signal to identify the systolic period.

24. The monitor of claim 23, wherein the calculation module is capable of identifying a moving minimum and moving maximum of a last moving average of the series of moving averages to identify the systolic period.

25. The monitor of claim 18, comprising a calculation module capable of calculating a moving average of a derivative of the pulse oximeter signal to generate a first output, calculating a moving average of the first output to generate a second output, calculating a moving average of the second output to generate a third output, and identifying a moving minimum and a moving maximum of the third output to identify the systolic period.

26. The monitor of claim 25, comprising a comparison module capable of comparing the moving minimum and the moving maximum to a scaled sum of the moving minimum and the moving maximum to determine the systolic period.

27. A tangible computer-readable medium, comprising:

code capable of identifying a systolic period of a pulse oximeter signal, wherein identifying a systolic period comprises calculating a moving average;

code capable of performing pulse qualification tests to qualify the systolic period for oxygen saturation calculations;

code capable of determining a strength of the systolic period if the systolic period is qualified for oxygen saturation calculations;

code capable of identifying a signal-to-noise ratio by comparing the strength of the systolic period to a measured value of a noise component of the pulse oximeter signal; and code capable of controlling the drive current based at least in part upon a comparison of the signal-to-noise ratio to a threshold.

28. The tangible computer-readable medium of claim 27, comprising code capable of measuring the noise component of the pulse oximeter signal.

29. The tangible computer-readable medium of claim 27, comprising code capable of calculating a moving average of a derivative of the pulse oximeter signal to generate a first output, calculating a moving average of the first output to generate a second output, calculating a moving average of the second output to generate a third output, and identifying a moving minimum and a moving maximum of the third output to identify the systolic period.

* * * * *